(12) United States Patent
Kirkpatrick

(10) Patent No.: US 8,668,671 B2
(45) Date of Patent: *Mar. 11, 2014

(54) AUTOMATIC LOADING OF IV PUMP CASSETTE

(75) Inventor: Gregg Kirkpatrick, Fallbrook, CA (US)

(73) Assignee: Carefusion 303, Inc., San Diego, CA (US)

( * ) Notice: Subject to any disclaimer, the term of this patent is extended or adjusted under 35 U.S.C. 154(b) by 413 days.

This patent is subject to a terminal disclaimer.

(21) Appl. No.: 12/869,577

(22) Filed: Aug. 26, 2010

(65) Prior Publication Data

US 2012/0053520 A1 Mar. 1, 2012

(51) Int. Cl.
*A61M 1/00* (2006.01)

(52) U.S. Cl.
USPC ............................................. 604/151

(58) Field of Classification Search
USPC .............. 604/80, 81, 151, 131; 335/289–294; 269/8
See application file for complete search history.

(56) References Cited

U.S. PATENT DOCUMENTS

| | | | | |
|---|---|---|---|---|
| 2,642,999 A * | 6/1953 | McPherson | | 211/65 |
| 3,982,716 A * | 9/1976 | Trees | | 248/309.4 |
| 4,038,982 A * | 8/1977 | Burke et al. | | 604/65 |
| 4,460,358 A * | 7/1984 | Somerville et al. | | 604/250 |
| 5,246,422 A | 9/1993 | Favre | | |
| 5,302,093 A * | 4/1994 | Owens et al. | | 417/474 |
| 5,364,364 A * | 11/1994 | Kasvikis et al. | | 604/151 |
| 5,665,070 A | 9/1997 | McPhee | | |
| 6,608,539 B2 * | 8/2003 | Nobutoki et al. | | 335/78 |
| 6,623,470 B2 * | 9/2003 | Munis et al. | | 604/503 |
| 7,772,948 B2 * | 8/2010 | Grow et al. | | 335/285 |
| 2005/0033245 A1 * | 2/2005 | Abrahamson et al. | | 604/250 |
| 2007/0270765 A1 * | 11/2007 | Hasler | | 604/246 |
| 2008/0097319 A1 | 4/2008 | Shih et al. | | |
| 2009/0125014 A1 * | 5/2009 | Bouthillier et al. | | 606/34 |
| 2010/0071192 A1 * | 3/2010 | Sarh et al. | | 29/525.06 |
| 2010/0256715 A1 * | 10/2010 | Hansen et al. | | 607/107 |

* cited by examiner

*Primary Examiner* — Nicholas Lucchesi
*Assistant Examiner* — Jenna Zhang
(74) *Attorney, Agent, or Firm* — McDermott Will & Emery LLP

(57) ABSTRACT

An intravenous (IV) pump system is disclosed. The IV pump includes a pumping segment and an IV pump. The pumping segment comprises a receptacle configured to hold a medical fluid and an alignment feature attached to the receptacle. The alignment feature comprises one of a magnetic or a magneto-sensitive material. The IV pump includes a housing having a shaped cavity configured to accept the alignment feature of the pumping segment and an attraction element comprising the other of the magnetic or the magneto-sensitive material. The attraction element is configured to attract the alignment feature toward the shaped cavity.

29 Claims, 7 Drawing Sheets

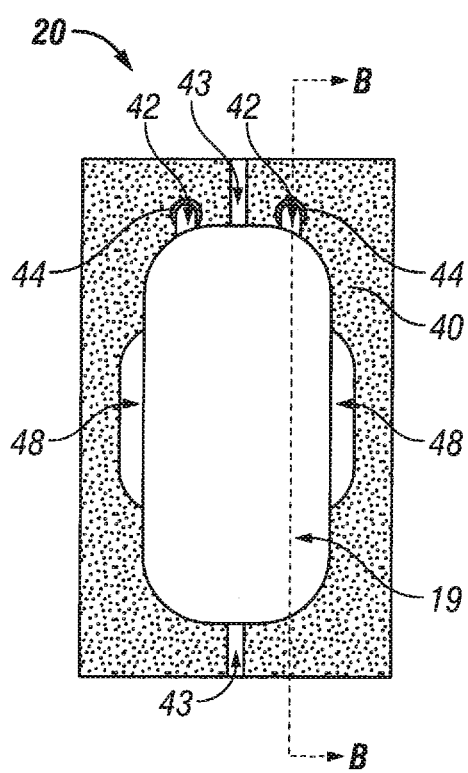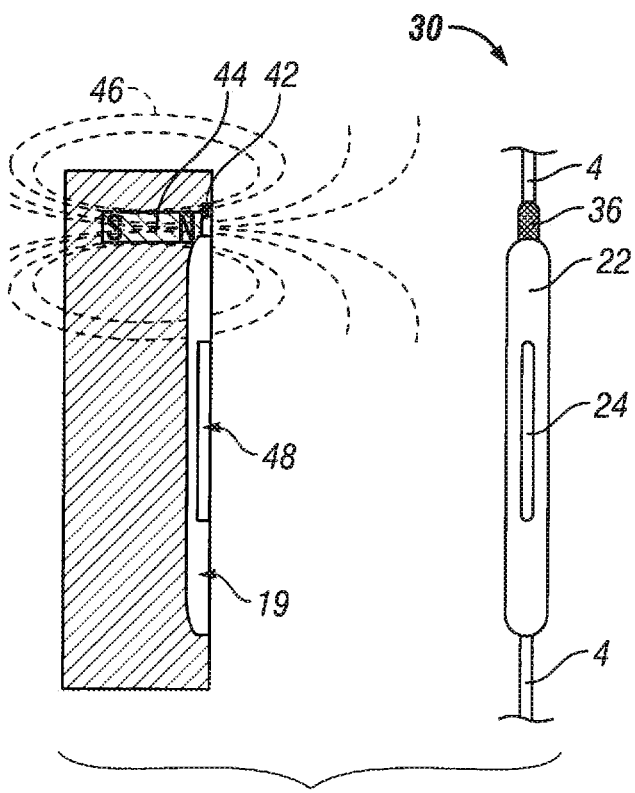
FIG. 8A  FIG. 8B
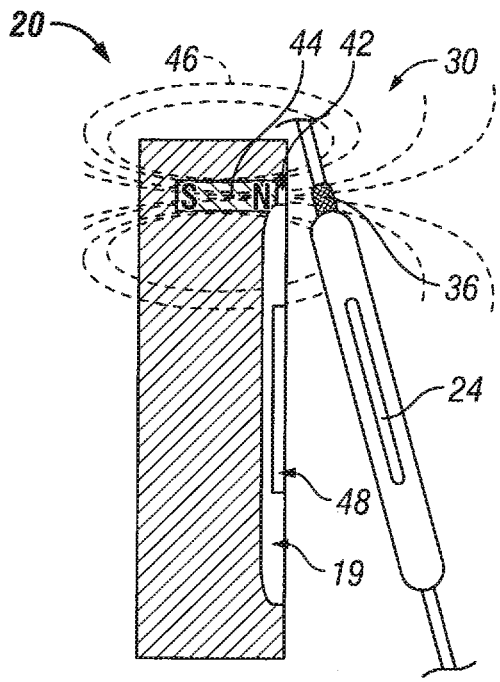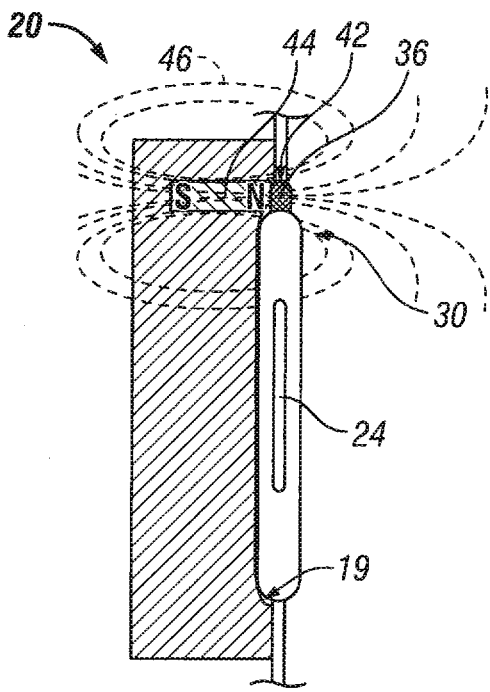
FIG. 8C  FIG. 8D

AUTOMATIC LOADING OF IV PUMP CASSETTE

BACKGROUND

1. Field

The present disclosure generally relates to administration of medical fluid by infusion and, in particular, relates to loading and preparation of infusion pumps.

2. Background

Infusion pumps have become commonplace within the healthcare world as a way to precisely administer intravenous (IV) fluids. Use of a pump in place of a simple roller clamp with an elevated fluid container to control the flow of the IV fluid allows more accurate and consistent control of the rate of delivery of the fluid to a patient.

The assembly of tubing, valves, fittings, and needles that connect the fluid container to the patient may be referred to as an "IV set." IV sets designed for use with IV pumps may have a pumping segment or chamber incorporated into the set, wherein the pumping segment fits into a compartment in the IV pump, as shown in FIG. 1. In use, medical fluid passes from the IV fluid container 14 through the tubing of IV set 18 to an infusion needle inserted in the arm of patient 10. The IV set 18 passes through a pumping module 20 of IV pump 12 that contains actuators (not shown) that act upon the pumping segment under the control of control unit 16 to force the medical fluid to flow to the patient 10 at a specified rate.

It is important that the pumping segment be properly positioned within the compartment of the IV pump to ensure that the actuators of the pumping module interact correctly with the pumping segment so that fluid is accurately pumped to the patient. Loading existing IV sets into an IV pump requires careful attention by the nurse or other healthcare provider to ensure that the pumping segment is properly positioned, as the various components and features of the IV set must be manually positioned within the pump and may slip out of position while the compartment door of the IV pump is being closed.

SUMMARY

The IV pump cassette and system disclosed herein enables a user to load an IV set having a pumping segment into an IV pump with significantly less effort and with greater assurance that the pumping segment is properly loaded. This enhancement of the loading process increases the safety of the patient while reducing the workload of the nurse. In other environments where the caregiver may not be a nurse, such as self-administered IV medical fluids at home, the automatic load feature of this IV pump cassette provides an increased level of confidence that the IV cassette is correctly loaded.

Certain exemplary embodiments of the present disclosure include an IV pump system comprising a pumping segment and an IV pump. The pumping segment comprises a receptacle configured to hold a medical fluid and an alignment feature attached to the receptacle, wherein the alignment feature comprises one of a magnetic or a magneto-sensitive material. The IV pump includes a housing with a shaped cavity configured to accept the alignment feature of the pumping segment, and an attraction element attached to the housing. The attraction element comprising a magnetic or, when the alignment features comprises a magnetic material, a magneto-sensitive material, and is configured to attract the alignment feature toward the shaped cavity.

In another embodiment, an IV pump arrangement is disclosed that includes a pump with a housing, a pumping segment separate from the housing, and a magnetic coupling connected to the pump and to the pumping segment. The magnetic coupling includes magnetically attractive elements respectively located on the pump and the pumping element configured to magnetically couple the pumping segment to the pump.

In another embodiment, a pumping segment is disclosed that comprises a body, an inlet, an outlet, a receptacle configured to hold a medical fluid and fluidically coupled to the inlet and the outlet, and an alignment feature attached to the body. The receptacle is configured to be manipulated to cause fluid to flow into the receptacle through the inlet and flow out of the receptacle through the outlet. The alignment feature comprises a magnetic or a magneto-sensitive material.

A method of automatically loading a pumping segment into an IV pump is disclosed. The method includes the steps of bringing a pumping segment having an alignment feature comprising a first material into proximity with an IV pump having a shaped cavity that is configured to accept the alignment feature, the IV pump having an attractive element comprising a second material that is magnetically attracted to the first material, the attractive element configured to attract the alignment feature toward the shaped cavity, allowing the attractive element to attract the alignment feature into the shaped cavity, seating the alignment feature in the shaped cavity such that the pumping segment is loaded in a predetermined position in the IV pump; and detecting that the pumping segment is correctly loaded in the IV pump.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 8A is a front view of a pump module of an IV pump according to certain embodiments of the present disclosure.

FIG. 8B-8D depict three sequential stages of loading the pumping segment of FIG. 6A into the pump module of FIG. 5A according to certain embodiments of the present disclosure.

DETAILED DESCRIPTION

IV pumps are frequently configured to accept a portion of a disposable IV set and to provide the pumping action through manipulation of this portion of the IV set so that IV pump mechanisms are not exposed to the fluid being pumped. This avoids the risk of exposure of the healthcare provider to the medication or blood product that is being administered as well as reducing the risk of infection of the patient. Some configurations of IV pumps use IV sets having a pumping segment that fits into the IV pump wherein the IV pump manipulates the pumping segment to pump the fluid. Careful attention by the nurse is required to correctly load the pumping segment into the IV pump and verify that the pumping segment is properly seated within the IV pump.

Certain exemplary embodiments of the present disclosure include an IV pump system comprising a pumping segment having an alignment feature comprising one of a magnetic or a magneto-sensitive material and an IV pump having a shaped cavity and an attraction element comprising a magnetic or, when the alignment features comprises a magnetic material, a magneto-sensitive material and configured to attract the alignment feature toward the shaped cavity.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

While the following discussion is directed to the loading of a pumping segment into an IV pump by a nurse, the disclosed methods and configurations may be used with other types of infusion systems and by other individuals.

Figure 1:
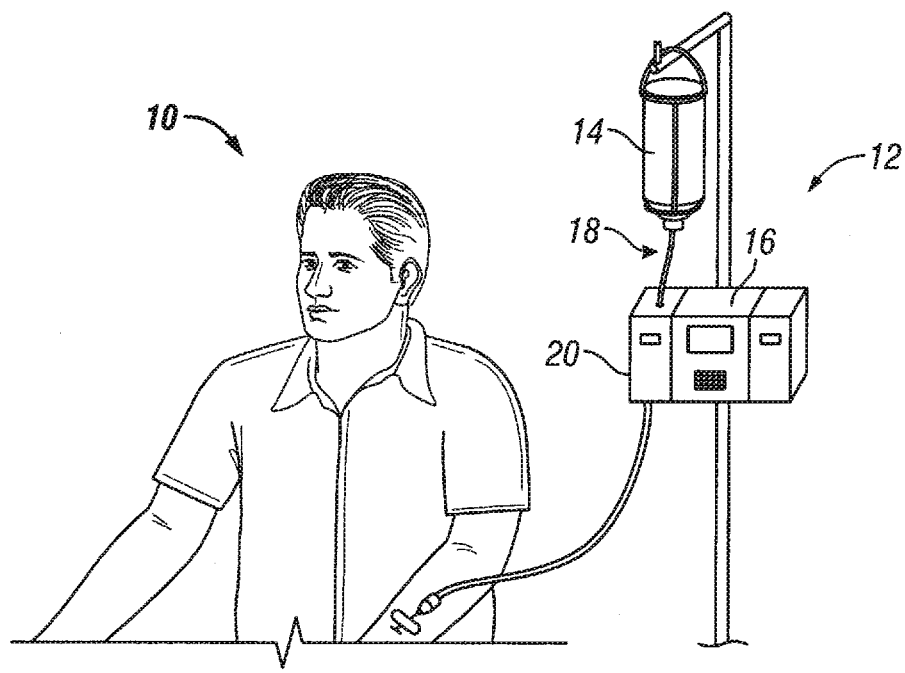
FIG. 1 depicts a patient receiving medical fluid through an IV set using an IV pump.

FIG. 1 depicts a patient 10 receiving medical fluid through an IV set 18 using an IV pump 12. The fluid is provided, in this example, in a flexible bag 14 that is commonly hung above the pump 12 to provide a positive pressure at the pump inlet. The IV pump 12 shown herein has a control unit 16 and an attached pumping module 20. The IV set 18 connects the fluid container 14 to the patient 10, and passes through the pumping module 20. The flow rate of the medical fluid is controlled by the pumping action of pumping module 20 under the control of control unit 16.

Figure 2:
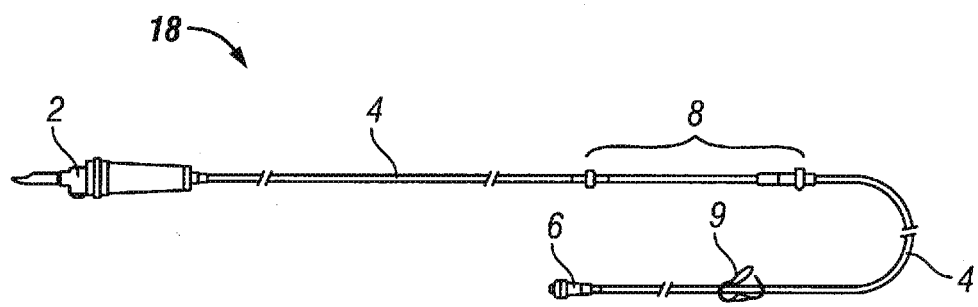
FIG. 2 depicts the construction of an example IV set.

FIG. 2 depicts the construction of an example IV set 18. This IV set 18 is set up for use with a peristaltic pump and the pumping segment that fits into the peristaltic pump is the length of tubing and fitting indicated by bracket 8. A length of tubing 4 is attached to each end of the pumping segment 8. A bag spike 2 is attached to the other end of one length of tubing 4, wherein a bag spike is a standard IV fitting configured to attach to a IV bag and puncture a seal that is part of the connection fitting on the IV bag. An alternate connection is a needleless Luer fitting or other type of fluid connector adapted for connection to a fluid source. At the other end of the other length of tubing 4, in this example, is a needleless Luer connector 6 that is suitable for connection to an infusion needle, such as shown in FIG. 1. In certain embodiments, other types of connectors and devices are attached in place of Luer connector 6. Also shown is a clamp 9 that, when closed completely, blocks flow through the tube 4 to which the clamp 9 is attached. This is frequently used to prevent flow and spillage while setting up or removing a IV set 18 from a pump. In certain embodiments, other types of fitting and connectors are added to create a multitude of other configurations of IV sets, depending on the application and type of treatment.

Figure 3:
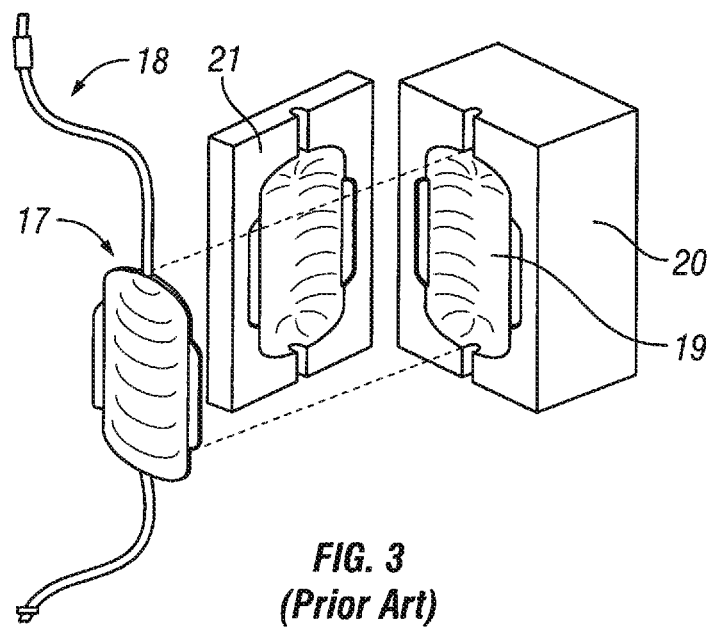
FIG. 3 illustrates a pumping segment of an IV set fitting into the pump module of the IV pump of FIG. 1.

FIG. 3 illustrates a pumping segment 17 of IV set 18 fitting into the pump module 20 of the IV pump 12 of FIG. 1. Pump module 20 has a cavity 19 that accepts pumping segment 17. Pumping segment 17 must be manually aligned and attached to cavity 19. Door 21 closes over the cavity 19 to capture the pumping segment 17. Internal mechanisms (not shown) of pump module 20 will manipulate pumping segment 17 to pump fluid from flexible bag 14 to the patient 10 of FIG. 1.

Figure 4:
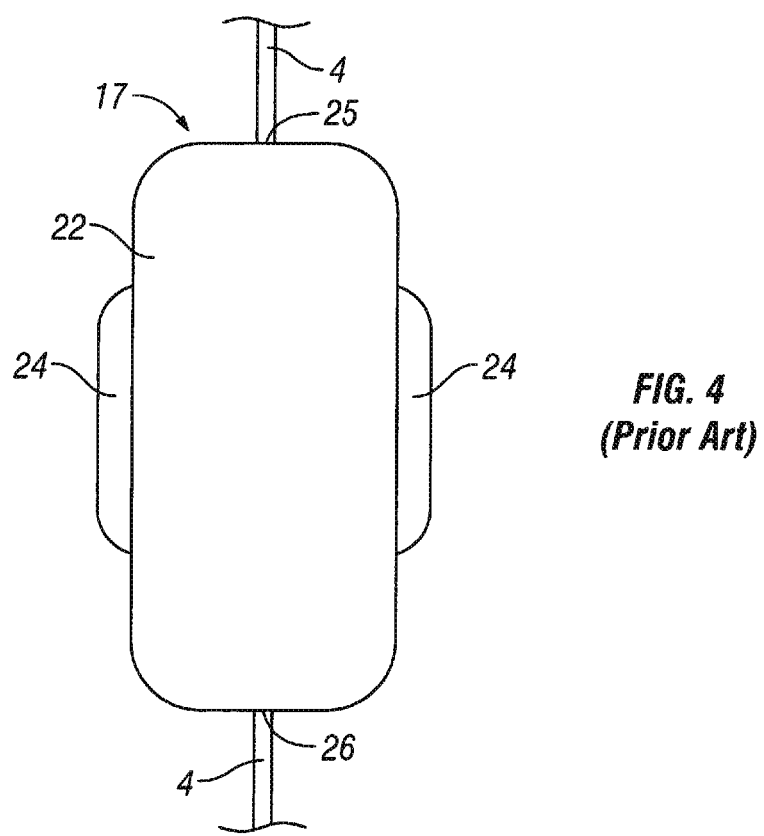
FIG. 4 illustrates the pumping segment of the IV set of FIG. 3 in more detail.

FIG. 4 illustrates the pumping segment 17 of the IV of FIG. 3 in more detail. In this example, the body of pumping element 17 comprises a receptacle 22 having an inlet 25 and an outlet 26. The receptacle is commonly formed from two sheets of a flexible plastic, bonded around the periphery to form a sealed compartment between the two sheets. In certain embodiments, the sheets are flat while in other embodiments, the sheets are shaped. Fittings are bonded between the sheets along the edges. Lengths of tubing 4 are attached to both the inlet 25 and the outlet 26 in this example. This example configuration of pumping element has a flat solid wing 24 on each side of receptacle 22. These wings 24 are captured by pumping element 20 and serve to hold the sides of receptacle 22 in place as the receptacle 22 expands and contracts during manipulation by pumping module 20.

Figure 5A:
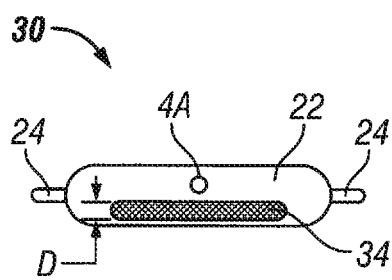
FIGS. 5A-5C are a top view, front view, and enlarged perspective view, respectively, of an embodiment of a pumping segment according to certain embodiments of the present disclosure.
Figure 5B:
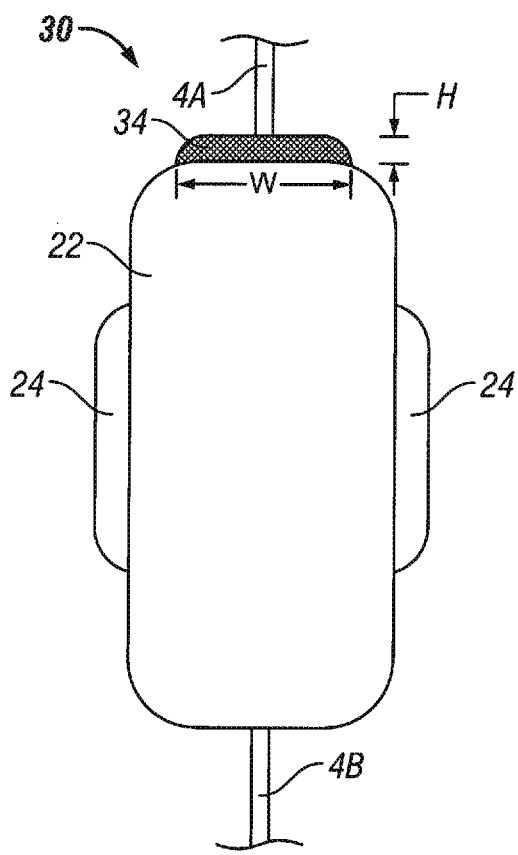
Figure 5C:
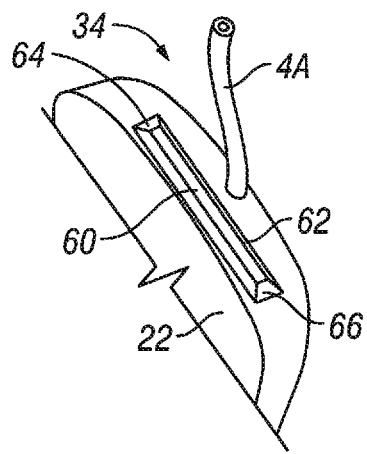

FIGS. 5A-5C are a top view, front view, and enlarged perspective view, respectively, of an embodiment of a pumping segment 30 according to certain embodiments of the present disclosure. The pumping segment 30 includes a receptacle 22 that forms a sealed container for medical fluid. Fluid flows from tube 4A at the top of pumping segment 30 into receptacle 22 and out through tube 4B at the bottom of pumping segment 22. Pumping segment 30 is a disposable element, to be coupled to a IV pump, such as IV pump 12, for use in administering the medical fluid to patient 10 of FIG. 1. In certain embodiments, receptacle 22 is a single volume. In certain embodiments, receptacle 22 comprises a plurality of pumping chambers. In other embodiments, receptacle 22 may comprise other types of pumping mechanisms without departing from the scope of the claims. Attached to receptacle 22 is an alignment feature 34. This alignment feature comprises either a magnetic material or a material that is attracted by a magnetic field, referred to herein as "magneto-sensitive." In certain embodiments, the alignment feature is fabricated entirely from the magnetic or magneto-sensitive material. In certain embodiments, the magnetic or magneto-sensitive material is mixed into a structural matrix such as a plastic and molded into a variety of shapes. In certain embodiments, the magnetic or magneto-sensitive material is applied as a coating to a non-magneto-sensitive substrate. Magnets may be formed from many ferromagnetic materials as well as other compounds that include iron oxides, such as ceramic magnets comprising iron and barium or strontium oxides, and materials that can have their atomic structure aligned, such as rare earth magnets comprising samarium-cobalt and neodymium-iron-boron.

In the embodiment of FIGS. 5A-5B, the alignment feature 34 is approximately a rectangular solid having a depth D, indicated in FIG. 5A, that is less than the height H of the alignment feature, indicated in FIG. 5B. The alignment feature 34 also has a width W, indicated in FIG. 5B, that is 5× greater than the height H of the alignment feature 34. In other embodiments, the ratio of depth-to-height and width-to-height vary. The alignment feature 34 is attached to the material of receptacle 22 through one or more of the processes of bonding, capturing the alignment feature 34 between sheets of flexible material that also form the receptacle 22, or mechanically attached using any of a variety of techniques known to those of ordinary skill in the art. In certain embodiments, alignment features 34 are formed by coating a portion of receptacle 22 with a magnetic or magneto-sensitive material.

FIG. 5C is a top perspective view of the alignment feature 34 where it can be seen that faces 60 and 62 are sloped with respect to each other, as are faces 64 and 66. In this embodiment, the edges along the top are sharp while the edges above surfaces 64 and 66 are rounded. In other embodiments, these edges are rounded while in other embodiments, these edges have sharp corners. In certain embodiments, faces 60 and 62 are parallel while in other embodiments, faces 64 and 66 are parallel.

Figure 6A:
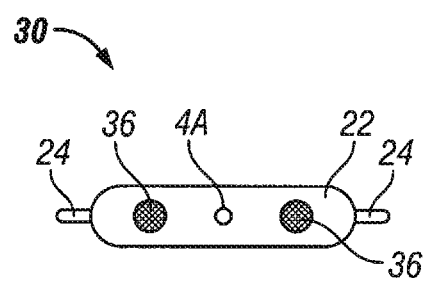
FIGS. 6A-6C are a top view, front view, and enlarged perspective view, respectively, of an alternate embodiment of a pumping segment according to certain embodiments of the present disclosure.
Figure 6B:
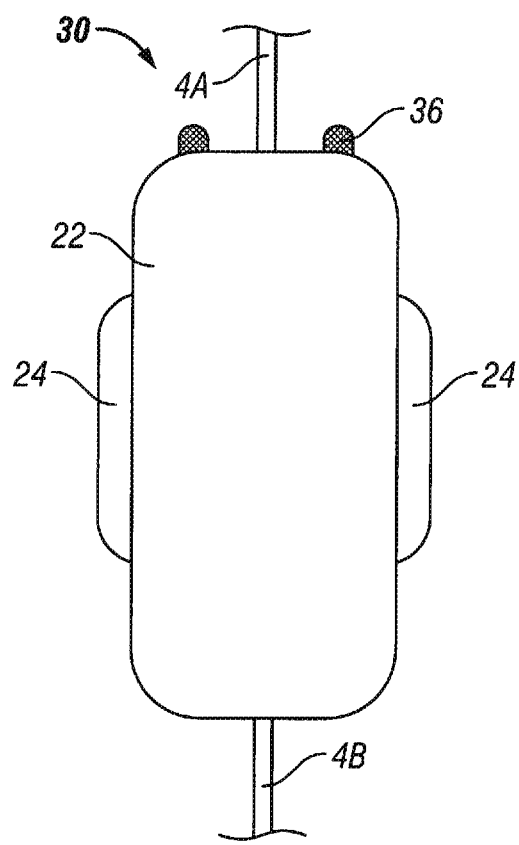
Figure 6C:
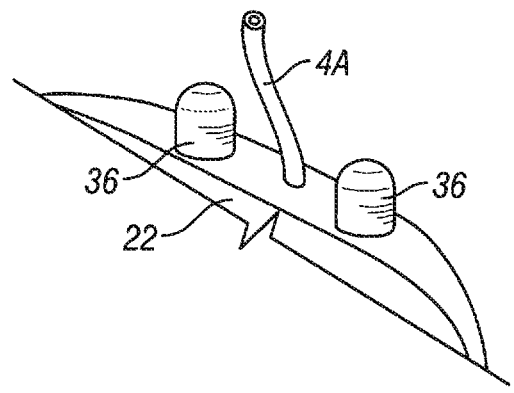

FIGS. 6A-6C are a top view, front view, and enlarged perspective view, respectively, of an alternate embodiment of pumping segment 30 according to certain embodiments of the present disclosure. This embodiment of pumping segment 30 comprises two alignment features 36 attached to receptacle 32. In this embodiment, alignment features 36 are substantially cylindrical posts with rounded tops. Alignment features 34 have other shapes or profiles in other embodiments. In the configuration of FIGS. 4A-4B, the alignment features 36 are symmetric about the IV line 4A. In other embodiments, the alignment features 36 may be asymmetric with respect to IV line 4A to prevent the pumping segment 30 from being loaded incorrectly.

FIG. 6C is a perspective view of the top region of pumping element 34, wherein it can be seen that alignment features 36 have rounded tops and are located symmetrically about tube 4A. In other embodiments, the tops of alignment features 36 are less rounded and, in some embodiments, sharp-edged. Other shapes and configurations of alignment feature will be apparent to those of ordinary skill in the art.

Figure 7:
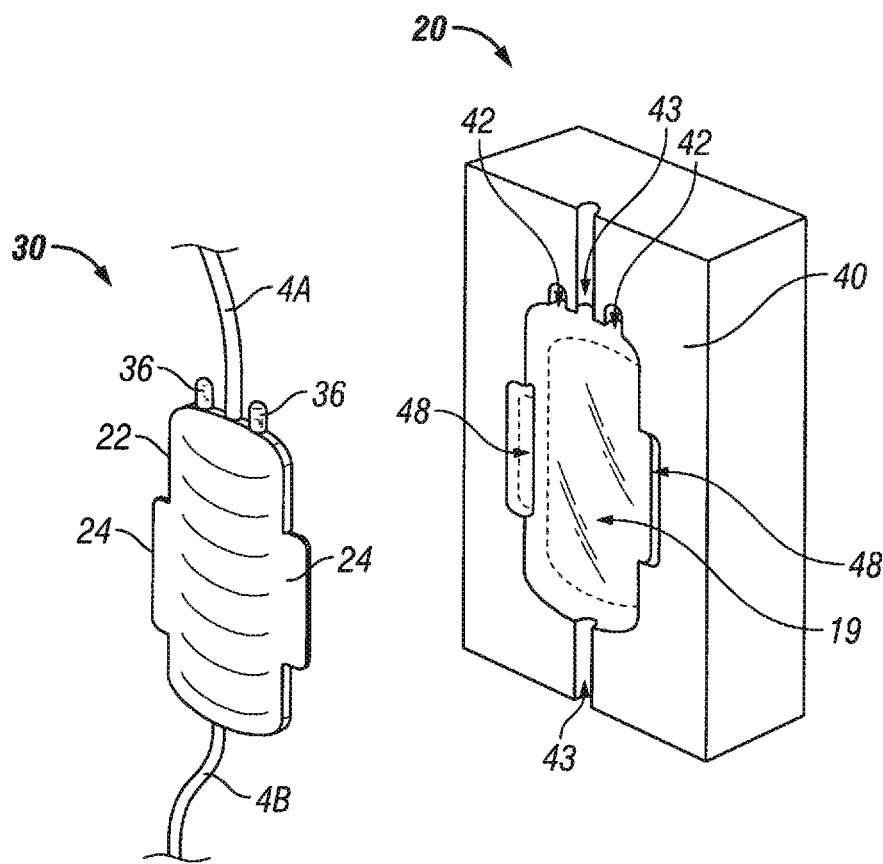
FIG. 7 depicts a pumping segment having alignment features of FIG. 6A fitting into a shaped cavity of a pumping module according to certain embodiments of the present disclosure.

FIG. 7 depicts a pumping segment 30 having alignment features 36 of FIG. 6A fitting into a shaped cavity 19 of a pumping module 20 according to certain embodiments of the present disclosure. Alignment feature 36 fit into shaped cavities 42, which located the remaining features of pumping element 20 in the correct position with respect to the mating elements of these features. Wings 24 are captured and held, in this example, in recesses 48 on each side of cavity 19. Tubes 4A and 4B fit into slots 43. A lid, now shown for clarity, is attached to body 40 of pump module 20 and closes over pumping element 30 after pumping element 30 is fully seated in pumping module 20.

FIG. 8A is a front view of the pump module 40 of an IV pump 12 according to certain embodiments of the present disclosure. Pump module 40 has a cavity 19 that, in this configuration, has two additional shaped cavities 42 that match the shapes and locations of alignment features 36 of FIG. 6A-6B. Co-located with shaped cavities 42 are attractive elements 44. In this embodiment, attractive elements 44 are cylindrical permanent magnets.

FIG. 8B-8D depict three sequential stages of loading the pumping segment 30 of FIG. 6A into the pump module 20 of FIG. 5A according to certain embodiments of the present disclosure. In FIG. 8B, magnetic field lines 46 are illustrative of the magnetic field generated by the magnets that form the attractive elements 44. Cavity 19, a recess 48, and a shaped cavity 42 can be seen in this cross-section, taken along the dashed line B-B in FIG. 8A. In pumping element 30, the receptacle 22 can be seen in profile, with one wing 24 visible on the near side and one alignment feature 36 visible in this view. In this embodiment, alignment feature 36 comprises a magneto-sensitive material. In other embodiments, this material is a material that is permanently magnetized. In this embodiment, the magneto-sensitive material is incorporated into the structure of the alignment features 36. In other embodiments, the magnetic or magneto-sensitive material is applied as a coating to the surface of the alignment features 36. In certain embodiments, attractive element 44 comprises an electromagnet that creates the magnetic field 46. In certain embodiments, both alignment features 36 and attractive elements 44 are magnetic. In certain embodiments, alignment features 36 are magnetic and attractive elements 44 are magneto-sensitive.

In FIG. 8C, pumping element 30 has been moved into the magnetic field 46 of attractive elements 44, causing the alignment features 36 to be drawn towards the shaped cavities 42. The strength of the magnetic force should be enough to help guide the alignment features 36 into the shaped cavities 42 while remaining low enough to be easily removed without damage to the IV set 30. The total attractive force should be within the range of 0.1 to 10.0 pounds, and especially within the range of 0.5 to 2.0 pounds.

FIG. 8D depicts the pumping element 30 fully seated in pumping module 20, with the alignment features 36 located in shaped cavities 42 and held there by the attractive force of magnetic field 46 that is created by attractive elements 44. The receptacle 22 is properly located in cavity 19 and the wings 24 are properly located in recesses 48. The pumping element 30 will be held in this position by the magnetic force to assist in setting up the IV pump.

In alternate embodiments, the alignment features 36 include magnetic material and the attractive elements 44 comprise the magneto-sensitive material, which produces the same attraction three. In other embodiments, both the alignment features 36 and the attractive elements 44 are magnetic. In yet other embodiments, the attractive elements 44 comprise electromagnetic elements, which offer the additional benefit of reducing the force required to remove the IV set by de-energizing the electromagnet.

Figure 9A:
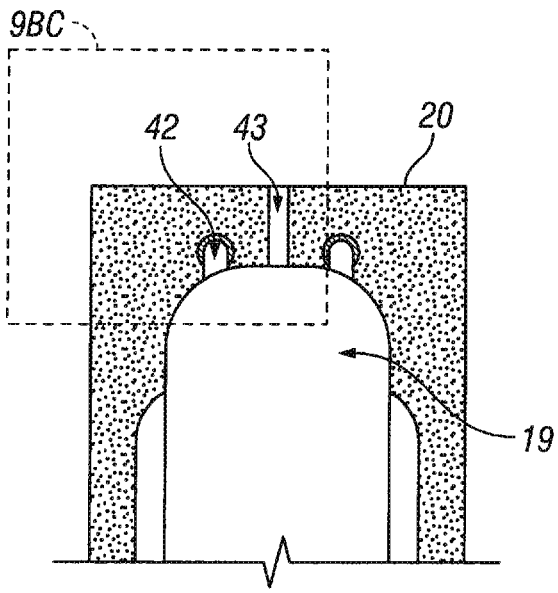
FIGS. 9A-9C illustrate two embodiments of arrangements for detecting that the pumping segment of FIGS. 6A-6B is properly seated in the pump module of FIG. 5A according to certain embodiments of the present disclosure.
Figure 9B:
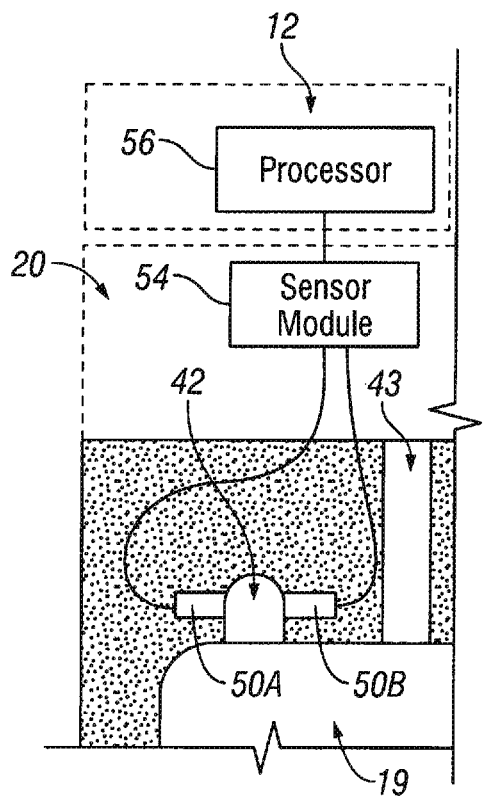
Figure 9C:
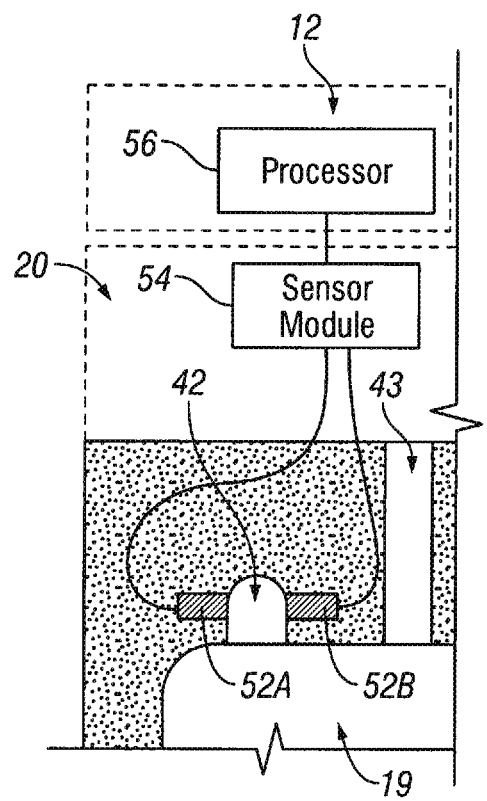

FIGS. 9A-9C illustrate two embodiments of arrangements for detecting that the pumping segment 30 of FIGS. 6A-6B is properly seated in the pump module 20 of FIG. 5A according to certain embodiments of the present disclosure. FIG. 9A is a repeat of a portion of FIG. 8A, with dashed line box 9BC indicating the region that is enlarged in FIGS. 9B and 9C.

FIG. 9B depicts a pair of optical sensors 50A and 50B installed on opposite sides of shaped cavity 42 such that an optical path exists between optical sensor 50A and 50B. When alignment feature 36 is seated in shaped cavity 42, this optical path is blocked and sensor module 54 will detect this condition and send a signal to processor 56 of the IV pump 12 to convey the information that the pumping segment 32 is properly located.

FIG. 9C depicts an embodiment wherein a pair of electrical sensors 52A and 52B have been installed on the side of shaped cavity 42, wherein there is a separation distance between the sensors 52A and 52B. In this example, the external surface of alignment feature 36 is conductive. An electrical circuit is formed between electrical sensor 52A and 52B when the alignment feature 36 is seated in shaped cavity 42B. Sensor module 54 will detect this continuity and send a signal to processor 56. Other types of sensors will be apparent to those of ordinary skill in the art, as will the ability to sense the proper seating of pumping segment 32 using other features of pumping segment 32.

Figure 10:
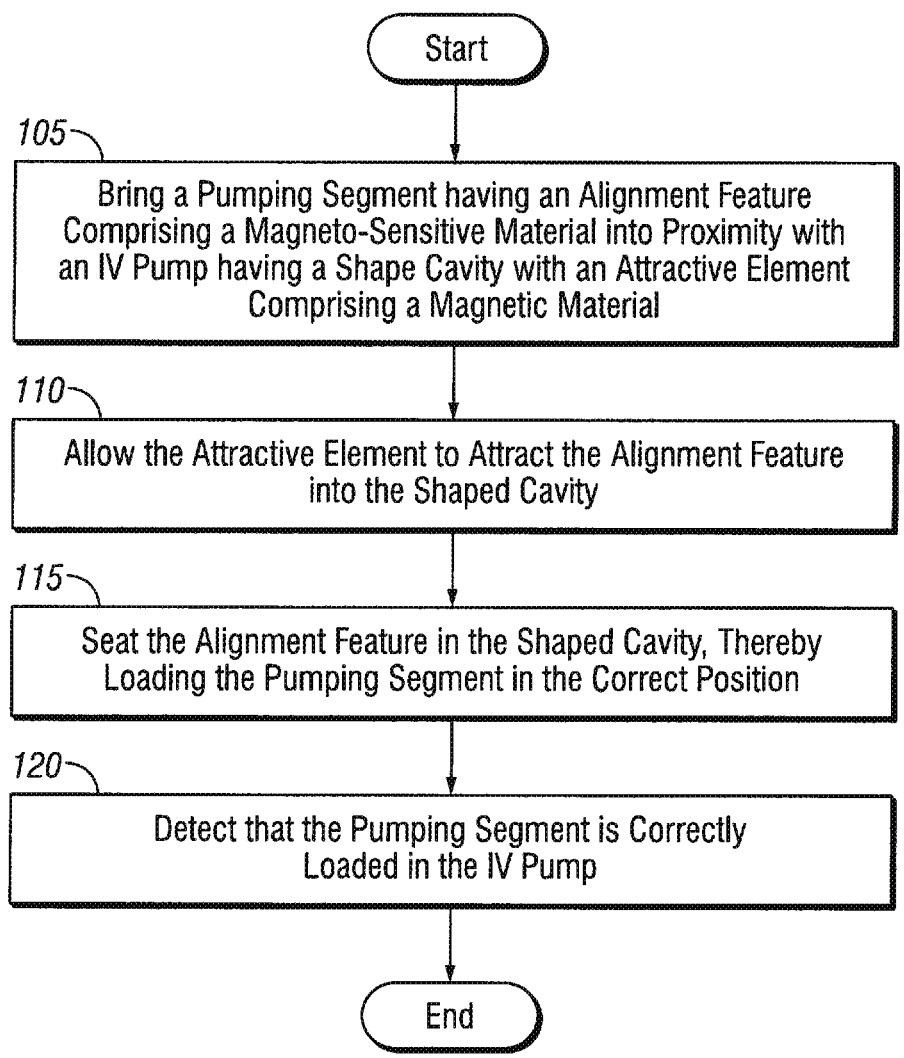
FIG. 10 is a flowchart depicting the process of loading a pumping segment of an IV set into an IV pump according to certain embodiments of the present disclosure.

FIG. 10 is a flowchart depicting the process of loading a pumping segment 32 of an IV set 18 into an IV pump 12 according to certain embodiments of the present disclosure.

In step 105, a pumping segment 32 having an alignment feature 36 that comprises a magneto-sensitive material is brought into proximity with an IV pump 12 having a shaped cavity 42 that is configured to accept the alignment feature 36. The shaped cavity 42 comprises an attractive element 44 that, in this example, is a magnetic material. In certain embodiments, the alignment feature 36 comprises a magnetic material and the attractive element 44 comprises a magneto-sensitive material. In step 110, the attractive feature 44 draws the alignment feature 36 into the cavity along with the pumping segment 32. In step 115, the alignment feature 36 is seated in the shaped cavity 42, causing the pumping element 32 to be seated in the proper location within the IV pump 12. In step 120, the IV pump 12 detects that the pumping segment is properly loaded into the IV pump. The load process is then complete and the nurse proceeds to configure the IV pump 12 and administer medical fluid to the patient 10.

It can be seen that the disclosed embodiments of the IV pumping system provide an improved method of guiding the installation of a pumping segment 32 of an IV set 18 into an IV pump 12. The force created by the magnetic attraction between the alignment features 36 of the pumping segment 32 and the attractive elements 44 of IV pump 12 draw the pumping segment 32 toward the proper operational position. This magnetic force is provided, in various embodiments, by a number of combinations of magnetic and magneto-sensitive materials used in the pumping segment 32 and the attractive elements 44. The addition of sensors such as optical sensors 50A and 50B provide additional assurance that the pumping segment 32 is located in the predetermined location within the IV pump 12.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

The term "magneto-sensitive" is used herein to refer to a material that is attracted by a magnetic field and may or may not be magnetized. Example of magneto-sensitive materials include ferromagnetic materials such as iron, some steels, nickel, and cobalt and ferrites such as barium ferrite BaO:6Fe$_2$O$_3$. Iron, for example, may be magnetized or unmagnetized. Unmagnetized iron is attracted by a magnetic field but does not generate its own magnetic field. Pairs of materials will be attracted to each other if the first material is magnetized and the second material is a magneto-sensitive material, which implies that the second material may be magnetized as well. Two non-magnetized magneto-sensitive materials will not be attracted to each other.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. An intravenous (IV) pump system, comprising:
   a pumping segment comprising:
      a receptacle configured to hold a medical fluid; and
      an alignment feature attached to the receptacle, the alignment feature comprising one of a magnetic or a magneto-sensitive material; and
   an IV pump comprising:
      a housing;
      a shaped cavity formed in the housing, the shaped cavity configured to accept the alignment feature of the pumping segment and retain the alignment feature in a fixed position with respect to the housing during operation of the IV pump; and
      an attraction element attached to the housing, the attraction element comprising a magnetic or, when the alignment features comprises a magnetic material, a magneto-sensitive material, wherein the attraction element and the shaped cavity are configured such that the alignment feature is guided toward a predefined position within the shaped cavity by the attraction element attracting the alignment feature toward the shaped cavity.

2. The IV pump system of claim 1, wherein the alignment feature comprises a magneto-sensitive material and the attraction element comprises a magnetic material.

3. The IV pump system of claim 2, wherein the magneto-sensitive material is a coating on the surface of the alignment feature.

4. The IV pump system of claim 2, wherein the attraction element comprises an electromagnet.

5. The IV pump system of claim 1, wherein both the alignment feature and the attraction element comprise a magnetic material.

6. The IV pump system of claim 1, wherein:
the alignment feature is an approximate solid rectangle having a width, a height, and a depth; and
the alignment feature is attached to the receptacle along a face having width and depth.

7. The IV pump system of claim 6, wherein the depth is less than twice the height and the width is more than twice the height.

8. The IV pump system of claim 1, wherein:
the alignment feature is an approximate solid cylinder having a diameter and a height; and
the alignment feature is attached to the receptacle on a cylindrical face.

9. The IV pump system of claim 8, wherein the diameter is less than the height.

10. The IV pump system of claim 1, wherein the receptacle of the pumping segment has an upper end, and wherein the alignment feature is attached to the receptacle at the upper end.

11. The IV pump system of claim 1, wherein the magnetic or magneto-sensitive material of the IV pump exerts a force in the range of 0.1 to 10.0 pounds on the alignment feature.

12. The IV pump system of claim 11, wherein the magnetic or magneto-sensitive material of the IV pump exerts a force in the range of 0.5 to 2.0 pounds on the alignment feature.

13. The IV pump system of claim 1, wherein the IV pump further comprises a sensor configured to detect that the pumping segment is correctly loaded into the IV pump.

14. The IV pump system of claim 1, wherein the pumping segment further comprises a first fluid conduit and a second fluid conduit that are connected to the receptacle such that fluid may flow from the first fluid conduit into the receptacle and then from the receptacle into the second fluid conduit.

15. An IV pump arrangement comprising:
a pump with a housing;
a pumping segment separate from the housing, the pumping segment comprising a body and a pumping chamber; and
a magnetic coupling connected to the housing and to the pumping segment, the magnetic coupling comprising magnetically attractive elements respectively located on the housing and the pumping element, the magnetic coupling configured to guide the pumping segment toward a pre-defined position and to retain the body of the pumping segment in a fixed position with respect to the housing of the pump during operation of the pump.

16. The IV pump arrangement of claim 15, wherein:
the magnetically attractive element on the pump comprises the magnetic element; and
the magnetically attractive element on the pumping segment comprises the magneto-sensitive material.

17. The IV pump arrangement of claim 15, wherein the magnetic coupling exerts a force in the range of 0.1 to 10.0 pounds on the alignment feature.

18. The IV pump arrangement of claim 17, wherein the magnetic coupling exerts a force in the range of 0.5 to 2.0 pounds on the alignment feature.

19. The IV pump arrangement of claim 15, wherein the IV pump further comprises a sensor configured to detect that the pumping segment is correctly coupled to the pump.

20. A pumping segment for an IV pump comprising:
a body;
an inlet;
an outlet;
a receptacle formed in the body and configured to hold a medical fluid and fluidically coupled to the inlet and the outlet, wherein the receptacle is further configured to be manipulated to cause fluid to flow into the receptacle through the inlet and flow out of the receptacle through the outlet; and
an alignment feature attached to the body, the alignment feature comprising a magnetic or a magneto-sensitive material, wherein the alignment feature does not move with respect to the body when the receptacle is manipulated, and alignment feature guiding the pumping segment toward a pre-defined position and retaining the body in a fixed position with respect to the housing of the pump during operation of the pump.

21. The pumping segment of claim 20, wherein the alignment feature is an approximate solid rectangle.

22. The pumping segment of claim 20, wherein the alignment feature is an approximate solid cylinder.

23. The pumping segment of claim 20, wherein the body has a top region, and wherein the alignment feature is attached to the body within the top region.

24. The pumping segment of claim 20, further comprising a length of tubing having a first and a second end, wherein the first end is coupled to at least one of the inlet and the outlet.

25. The pumping segment of claim 24, further comprising a connection device coupled to the second end of the length of tubing.

26. The pumping segment of claim 20, wherein the body comprises a flexible sheet, wherein a portion of the body comprises two layers of the flexible sheet to form the receptacle.

27. A method for operating an intravenous pump, comprising the steps of:
bringing a pumping segment having a body and an alignment feature fixedly coupled to the body of the pumping element and comprising a first material into proximity with an IV pump having a body with a shaped cavity that is configured to accept the alignment feature, the IV pump comprising an attractive element that comprises a second material that is magnetically attracted to the first material, the attractive element configured to attract the alignment feature toward the shaped cavity;
allowing the attractive element to attract the alignment feature so as to guide the pumping segment toward the shaped cavity;
seating the alignment feature in the shaped cavity such that the alignment feature is held in a fixed position with respect to the body and the pumping segment is loaded in a pre-determined position in the IV pump; and
detecting that the pumping segment is correctly loaded in the IV pump.

28. The method of claim 27, wherein the first material is magneto-sensitive and the second material is magnetic.

29. The method of claim 27, wherein the first material is magnetic and the second material is magneto-sensitive.

* * * * *